(12) United States Patent
Balduf et al.

(10) Patent No.: US 7,495,129 B2
(45) Date of Patent: Feb. 24, 2009

(54) PURIFICATION OF A MONOMER BY EXTRACTION WITH A PHASE FORMER AND CRYSTALLIZATION

(75) Inventors: Torsten Balduf, Houston, TX (US); Stefan Nordhoff, Recklinghausen (DE); Dennis Thong Yu-Chiang, Marl (DE); Axel Kobus, Bochum (DE); Martin Roos, Haltern (DE)

(73) Assignee: Evonik Stockhausen GmbH, Krefeld (DE)

( * ) Notice: Subject to any disclaimer, the term of this patent is extended or adjusted under 35 U.S.C. 154(b) by 326 days.

(21) Appl. No.: 10/541,647

(22) PCT Filed: Jan. 13, 2004

(86) PCT No.: PCT/EP2004/000163

§ 371 (c)(1),
(2), (4) Date: Nov. 18, 2005

(87) PCT Pub. No.: WO2004/063134

PCT Pub. Date: Jul. 29, 2004

(65) Prior Publication Data

US 2006/0116532 A1 Jun. 1, 2006

(30) Foreign Application Priority Data

Jan. 13, 2003 (DE) .......................... 103 01 040

(51) Int. Cl.
*C07C 51/42* (2006.01)

(52) U.S. Cl. .................................................. 562/600

(58) Field of Classification Search ....................... None
See application file for complete search history.

(56) References Cited

U.S. PATENT DOCUMENTS

| 2,922,815 | A |   | 1/1960  | Faerber         |        |
|-----------|---|---|---------|-----------------|--------|
| 3,657,332 | A |   | 4/1972  | Sennewald, et al.|       |
| 3,663,375 | A | * | 5/1972  | Witheford       | 203/15 |
| 3,846,488 | A |   | 11/1974 | Otsuki et al.   |        |
| 3,932,500 | A |   | 1/1976  | Duembgen et al. |        |
| 3,997,599 | A |   | 12/1976 | Grinstead       |        |
| 4,143,066 | A |   | 3/1979  | Kalcevic        |        |
| 4,720,577 | A |   | 1/1988  | Wojtech et al.  |        |
| 4,780,568 | A |   | 10/1988 | Pascoe          |        |

(Continued)

FOREIGN PATENT DOCUMENTS

DE 863 050 1/1953

(Continued)

OTHER PUBLICATIONS

International Search Report mailed on Jun. 24, 2004 in connection with PCT/EP2004/000163.

*Primary Examiner*—Karl J Puttlitz
(74) *Attorney, Agent, or Firm*—Smith Moore Leatherwood LLP

(57) ABSTRACT

The invention concerns a process for purification of an acidic monomer having a double bond, as well as a device for synthesis of an acidic monomer having a double bond, a process for producing an acidic monomer having a double bond, an acid monomer having a double bond and obtainable by this process, fibers, formed bodies, films, foams, superabsorbent polymers and other special polymers based on or containing this acidic monomer, the use of this acidic monomer in or for producing fibers, formed bodies, films, foams, superabsorbent polymers or other special polymers.

10 Claims, 3 Drawing Sheets

U.S. PATENT DOCUMENTS

| | | | |
|---|---|---|---|
| 5,426,219 | A | 6/1995 | Lehnhardt et al. |
| 5,504,247 | A | 4/1996 | Saxer et al. |
| 5,523,480 | A | 6/1996 | Bauer, Jr. et al. |
| 5,780,276 | A | 7/1998 | Baniel |
| 5,831,124 | A * | 11/1998 | Machhammer et al. ..... 562/600 |
| 6,174,929 | B1 | 1/2001 | Hahnle et al. |
| 6,380,427 | B1 | 4/2002 | Miyazaki et al. |
| 6,448,439 | B1 | 9/2002 | Eck et al. |
| 2004/0116741 | A1 | 6/2004 | Nordhoff et al. |

FOREIGN PATENT DOCUMENTS

| | | |
|---|---|---|
| DE | 21 36 396 | 2/1973 |
| DE | 196 06 877 A1 | 8/1997 |
| EP | 0 616 998 A1 | 9/1994 |
| EP | 0 675 100 A2 | 10/1995 |
| EP | 0 792 867 B1 | 9/1997 |
| EP | 1 002 787 A1 | 5/2000 |
| WO | WO 99/14181 | 3/1999 |
| WO | WO 02/055469 | 7/2002 |

* cited by examiner

PURIFICATION OF A MONOMER BY EXTRACTION WITH A PHASE FORMER AND CRYSTALLIZATION

This application is a national stage application under 35 U.S.C. 371 of international application No. PCT/EP2004/000163 filed Jan. 13, 2004, which is based on German Application No. DE 103 01 040.8 filed Jan. 13, 2003, and claims priority thereto.

BACKGROUND OF THE INVENTION

The invention concerns a process for purification of an acidic monomer having a double bond, a device for synthesis of an acidic monomer having a double bond, a process for producing an acidic monomer having a double bond, an acidic monomer having a double bond and obtainable by this process, fibres, formed bodies, films, foams, superabsorbent polymers and other special polymers based on or containing this acidic monomer, the use of this acidic monomer in or for producing fibres, formed bodies, films, foams, superabsorbent polymers or other special polymers.

Due to the fact that mass produced synthetic materials are today increasingly used in areas in which high demands are made concerning hygiene and purity grade of the synthetic material, the provision of pure monomers for large-scale synthesis of synthetic materials becomes ever more important.

These demands on monomer purity, which are coming increasingly to the fore, correspond to monomer syntheses that are accordingly improved and lead to greater purity in ever-improved reactors and with new catalyst systems.

Despite the significant efforts in the area of reactor and catalyst research the crude monomer streams coming out of the reactors are still so impure, that these crude monomer streams must be subjected to a careful purification, before the thus obtained pure monomer can be worked into correspondingly pure synthetic materials by polymerization. The purification of the crude monomer stream in the technical production of monomers therefore takes on considerable importance.

Another parameter which is gaining increasing importance in the further development of technical syntheses of monomers and their treatment is the environmental aspect. In this context the use of water or aqueous systems is accorded great importance. Furthermore, the avoidance of waste as well as the achievement of higher yields with high conversions contributes to the environmental friendliness of technical syntheses. It is, therefore, important in technical syntheses of monomers to also recover and reuse quantities of monomer which seem small as a percentage proportion, which can form in many different flow-offs of the technical monomer synthesis, in order to optimise in this way the yield of the technical monomer synthesis.

An example of the currently described trend is the synthesis of water-absorbing polymers, which are used in hygiene articles such as diapers, sanitary napkins or incontinence articles. Very high demands on purity are made on these water-absorbing polymers. The demands on purity of the acrylic acids used in the production of these water absorbing polymers are therefore correspondingly high. Another example of technically produced polymers for which high demands on purity are made is the area of polymers used in treatment of drinking water. In this regard, non-cross-linked, linear polyacrylic acids are often concerned, which, by reason of the high demands on purity, are produced from acrylic acid which is as pure as possible.

U.S. Pat. No. 4,720,577 teaches the purification of low molecular carboxylic acids having no double bond, such as acetic acid, by use of an extraction auxiliary formed from aliphatic amines and phenol. The use of an extraction auxiliary comprising two components, the amine and the phenol, is complicated in comparison with a single component extraction auxiliary.

U.S. Pat. No. 3,997,599 discloses the purification of carboxylic acids such as methacrylic acid as aqueous phase by extraction with trioctylphosphine oxide in an organic solvent such as kerosene. The use of an organic solvent which is on the one hand environmentally polluting and is furthermore easily combustible is a disadvantage.

DE 21 36 396 teaches a purification of acrylic acid by counter-current washing with an extremely hydrophobic solvent, wherein organic solvents are preferably used as solvent, which carry an increased fire risk and environmental pollution.

DE 863 050 describes the purification of aqueous acrylic and methacrylic acids by extraction via addition of concentrated sulphuric acid, wherein an upper acrylic and methacrylic acid-rich phase forms. In this phase, however, a number of impurities such as benzaldehyde, propionic acid or dimeric acrylic and methacrylic acids also accumulates compared to the starting mixture used. This is disadvantageous for the large-scale application of this extraction.

In U.S. Pat. No. 3,663,375 discloses a three-step process for purification of a mixture containing isobutyric acid and methacrylic acid by salting out with sulphuric acid or sodium sulphate, wherein in a first step this mixture is salted out with formation of an aqueous and an organic phase, in a second step the phases are separated from each other and in a third step the separated phases respectively separated from each other are worked up by distillation. This teaching is disadvantageous on the one hand because of the many steps and on the other because of the thermally cumbersome distillation of monomers such as acrylic and methacrylic acids. During the distillation of acrylic and methacrylic acids dimers or oligomers of acrylic and methacrylic acids are particularly easily formed, which are undesirable in the large scale further processing into polymers.

DE 196 06 877 A1 discloses the extraction of an acidulous water side-stream with a small partial current of an almost acrylic acid-free solvent. The main stream of the acrylic acid gas stream obtained by gas phase oxidation is first worked up by absorption with a high boiling point solvent, followed by distillation and crystallization. The extraction disclosed here is disadvantageous through the use of the almost acrylic acid-free solvent and is not suitable for the main stream.

The general object of the present invention is, on the one hand, to overcome the disadvantages arising from the prior art.

On the other hand, an object according to the invention is to achieve, as inexpensively and environmentally friendly as possible and with a high yield, the extraction of the synthesised monomers from a mixture which contains further impurities in addition to the desired synthesised monomers.

Furthermore, it is an object of the invention consists to enable the purification of monomers with a phase former composed of as few components as possible.

An additional object according to the invention is to achieve purification of a monomer in as few steps as possible.

A further object according to the invention is, during purification of monomers, to deplete the various accompanying impurities simultaneously by a cleaning procedure, if possible.

A further object according to the invention lies in the provision of as gentle a monomer purification as possible, since the monomers are mostly reactive compounds and should be thermally stressed as little as possible.

SUMMARY OF THE INVENTION

The above-mentioned objects are solved by the category-forming claims below, wherein claims dependent from these category-forming claims describe preferred embodiments according to the invention.

In particular the invention is concerned with a process for purification of an acidic monomer having a double bond, comprising the steps
(a) providing a starting mixture, containing as starting mixture components, respectively based on the starting mixture,
  (a1) at least about 5 wt. %, preferably at least about 30 wt. % and particularly preferably at least about 60 wt % and even more preferably about 62 to about 90 wt. % of the acidic monomer and either
  (a2) at least about 0.01 wt. %, preferably at least about 1 wt. % and particularly preferably at least about 10 wt. % water, or
  (a3) at least about 0.01 wt. %, preferably at least about 0.1 and particularly preferably at least about 5 wt. % of a component of the starting mixture, or (a2) and (a3),
  wherein the sum of the wt. % proportions of the starting mixture components is respectively 100 wt. %;
(b) addition of a phase former which is preferably more hygroscopic in comparison with the acidic monomer or a salt of this phase former or a mixture of both by obtainment of a purification mixture, out of which
(c) at least a first phase and at least a further phase distinguished from the first phase by a phase boundary form a phase system;
(d) decrease in temperature of the phase system, wherein
(e) in one of the phases of the phase system a product crystal containing at least about 50 wt. %, preferably at least about 70 wt. % and particularly preferably about 90 wt. % as well as even more preferred at least about 95 wt. %, of one of the starting mixture components, preferably the acidic monomer, is formed in addition to another starting mixture component as a crystal system;
(f) isolation of the product crystals.

In a preferred embodiment of the process according to the invention the steps (c) and (d) occur at the same place, preferably in a common container, in a single step. In another preferred embodiment of the process according to the invention the steps (c) and (d) occur spatially separated from each other, preferably in at least two containers, with two or more steps.

A further embodiment according to the invention is that the steps (c) and (d) are not interrupted by further steps and therefore follow one immediately after the other.

In a further preferred embodiment of the process according to the invention the starting mixture has as starting mixture component (a3) at least about 1 wt. %, preferably at least about 15 wt. % and particularly preferably at least about 30 wt. % of at least one starting mixture component. This is particularly the case for various bottom products from a workup of the acidic monomer. Starting mixture components, preferably starting mixture component (a3), are preferably impurities which are different to the acidic monomers with the exception of water. The starting mixture components preferably possess a higher molecular weight than the monomers according to the invention. It can be furthermore preferred that the starting mixture components boil at least 5° C., preferably at least about 20° C. and particularly preferably at least about 40° C. higher than the acidic monomer. Oligomers of the acidic monomer frequently form a typical starting mixture component. By oligomers of the acidic monomer are understood here molecules which consist of at least two acidic monomer molecules. Further starting mixture components frequently occurring in the starting mixture are the reaction products accumulating during the synthesis and workup of the acidic monomer, preferably as described in the examples below.

DETAILED DESCRIPTION OF THE INVENTION

On the one hand, starting mixtures often accumulate in the bottom liquid of distillation columns when producing acidic monomers. Such a bottom-starting mixture contains as bottom-starting mixture components, respectively based on the bottom starting material mixture,
(a1S) at least about 5 wt. %, preferably at least about 50 wt. % and particularly preferably at least about 75 wt. % of an acidic monomer,
(a2S) at least about 0.05 wt. %, preferably at least about 2 wt. % and particularly preferably at least about 5 wt. % water,
(a3S) at least about 1 wt. %, preferably at least about 5 wt. % and particularly preferably at least about 10 wt. % of a starting mixture component, wherein the sum of the wt. % proportions of the bottom starting mixture components gives respectively 100 wt. %.

Furthermore, according to the process according to the invention, starting mixtures which are good to purify are frequently obtained in the heads of distillation columns in which the acidic monomers are distilled.

Such a head-starting mixture contains as head-starting mixture components, respectively based on the head-starting mixture,
(a1K) at least about 0.5 wt. %, preferably at least about 50 wt. % and particularly preferably at least about 75 wt. % of an acidic monomer,
(a2K) at least about 0.05 wt. %, preferably at least about 2 wt. % and particularly preferably at least about 5 wt. % water,
(a3K) at least about 0.5 wt. %, preferably at least about 1 wt. % and particularly preferably at least about 2 wt. % of a starting mixture component, wherein the sum of the wt. % proportions of the head-starting mixture components gives respectively 100 wt. %.

In addition, in the process according to the invention, advantageous starting mixtures which can be purified are obtained during the oligomer cracking. These oligomers of the acidic monomer form in various positions of the purification of currents containing acidic monomers. The formation of oligomers can moreover already occur during the synthesis of the acidic monomer. The oligomer formation can further occur by thermal purification of the acidic monomers by distillation. Moreover, it is often observed that oligomers of the acidic monomer accumulate in purification steps such as crystallization.

Such an oligomer-starting mixture originating from an oligomer cracker as bottom liquid contains the oligomer-starting mixture components as described above for the bottom liquid.

In addition, the purification of mixtures which contain at least one acidic monomer and water by crystallization limited by phase diagrams. In order to achieve a further enrichment of acidic monomers in these at least one acidic monomer and water containing mixtures, the process according to the invention can be used advantageously.

The consideration of the phase diagram of such an at least binary eutectic starting mixture, containing at least the acidic monomer as principal component and compared to the acidic monomer a second minor component, preferably water, has solid and liquid lines in a temperature/concentration phase diagram. Further details regarding the determination of the solidus and liquidus lines in a temperature/concentration phase diagram for various phase systems are described with further evidence in *"Theory and Application of Melt Crystallization"* promoted by the European Thematic Network CRYSOPT, 28/29 Sep. 2000 in Halle-Wittenberg Chapter 2 *"Phase Diagrams"* by Prof. Dr. Axel König, Universität Erlangen-Nürnberg. These solidus and liquidus lines have at least one S-L intercept point, at which point both lines cut or tangent each other. Characteristic phase diagrams, which can describe the phase diagrams according to the invention, are described in Atsuoka, M.: *"Developments in Melt Crystallization"*, Advances in Industrial Crystallization, J. Garside, R. J. Davey and A. G. Jones, Eds., Oxford (U.K.); Butterworth-Heinemann Ltd. (1991), pp. 229-244.

A eutectic starting mixture preferred according to the invention contains as eutectic starting mixture components the acidic monomer in a concentration range which from the at least one S-L intercept point +/− maximum 60%, preferably +/− maximum 30%, preferred +/− maximum 10% and particularly preferred +/− maximum 5%, unless concentrations of acidic monomer of less than 0 or more than 100% are obtained. The corresponding concentrations of minor components follow correspondingly from the phase diagram.

Preferred eutectic starting mixtures AA of acrylic acid, water and a starting mixture component different from water contain as eutectic starting mixture components based respectively on the eutectic starting mixture, (a1E) an acidic monomer, in the range from about 0.01 to about 99.99 wt. %, preferably in a range from about 15 to about 85 wt. % and particularly preferably in a range from about 40 to about 65 wt. %, (a2E) water, in the range from about 5 to about 95 wt. %, preferably in a range from about 10 to about 80 wt. % and particularly preferably in a range from about 30 to about 50 wt. %, (a3E) at least about 0.01 wt. %, preferably at least about 2 wt. % and particularly preferably at least 10 wt. % of a starting mixture component, wherein the sum of the wt. % proportions of the eutectic starting mixture components respectively gives 100 wt. %.

It is further preferred in the process according to the invention that the purification mixture has the phase former in a quantity in the range from about 1 to about 80 wt. %, preferably in the range from 10 to 50 wt. % and particularly preferably in the range from about 20 to about 30 wt. %.

It is additionally preferred to use the salt of the phase former as solutions, in which water is the preferred solvent. Such phase former salt solutions contain the phase former salt in a concentration in the range from about 1 to about 60 wt. %, preferably in the range from about 20 to about 55 wt. % and particularly preferably in the range from about 40 to about 50 wt. %, respectively based on the phase former salt solution.

It is also preferred in the process according to the invention that a Brönsted acid with a pH value of less than about 6, preferably less than about 3 and particularly preferably less than about 1, a salt of this Brönsted acid or a mixture thereof be used as phase former. Particularly preferred as Brönsted acids are acids which have atoms of the $5^{th}$ and $6^{th}$ main groups of the Periodic Table of the Elements, preferably phosphorus, sulphur or oxygen. Sulphuric acid and phosphoric acid as well as the alkali or alkaline earth metal salts of sulphuric acid or phosphoric acid have proved of particular value in this regard, whereby sulphuric acid, sodium hydrogensulphate or mixtures thereof is preferred.

It is further preferred in the process according to the invention that the phase former is liquid at time of addition. Thus phase formers which are available as liquids at 20° C. under normal conditions are particularly preferred.

By "hygroscopic" according to the invention is understood the affinity for water which is described in more detail and measured by means of a hygrometer in Römpp, Lexikon der Chemie, $10^{th}$ fully revised edition 1997, page 1858.

The extent and the type of temperature reduction in the process according to the invention depends on the characteristics of the liquidus and solidus lines of the respective temperature/concentration phase diagrams of the starting mixture to be separated. It is thus preferred that the temperature be reduced to below the liquidus line of a starting mixture component in the starting mixture. It is further preferred that the temperature be maintained above the solidus line. It is additionally preferred that the temperature be maintained within the range of the phase diagram defined by the solidus and liquidus lines. In the case of a eutectic it is further preferred that the temperature does not fall below the temperature of the S-L intercept point of the concentration range selected for the extraction, of the starting mixture component with the highest concentration.

It is additionally preferred according to the invention that after formation of the phase system, preferably after formation of the crystal system, at least a part of the phase former is recovered and added to the starting mixture in step (b) again. In the case that the crystal system has crystals of the acidic monomer, the phase former-enriched phase can, for example, be removed from respectively the phase system or the crystal system and added to the starting mixture in step (b) again after corresponding workup of the water-depleted phase former.

It is furthermore preferred in the process according to the invention that the phase system forms as a phase system at least a first liquid phase and an at least one further liquid phase distinguished from the first phase by means of a phase boundary. The first liquid phase is a water-poor liquid phase in comparison with the further liquid phase. It is furthermore preferred that the water-poor liquid phase possesses a lower density than the water-rich liquid phase. The density difference preferably amounts to at least about 10 kg/m$^3$, preferably at least about 100 kg/m$^3$ and particularly preferably at least about 200 kg/m$^3$. It is additionally preferred in the process according to the invention that the concentration of acidic monomer be higher in the water-poor phase in comparison with the concentration of acidic monomer in the water-rich phase. The individual starting mixture components can be separated from each other by separating the different liquid phases.

It is further preferred in the process according to the invention that the product crystals forming in one phase of the phase system consist predominantly of preferably at least about 80 wt. % and particularly preferably at least about 90 wt. % based on the product crystal respectively, acidic monomer or water.

To further increase the purification performance of the process according to the invention it is preferred that the crystal system or the isolated product crystal or both be subjected to a further purification step. As processes and devices which can be used in this further purification step or steps are mentioned all those familiar to and suitable for the person skilled in the art. Among these processes are preferred those that put only small thermal stress on the material to be purified. Crystallization processes such as layer crystallization and suspension crystallization belong particularly to these processes, wherein suspension crystallization is preferred. Crystallization products of the above-mentioned crystallization processes can further be subjected to a washing step. It can furthermore be advantageous that the crystals of the crystal phase be at least partially molten before the transfer to the further purification step.

Suitable processes for this are known from EP 0 616 998, WO 99/14181, U.S. Pat. No. 4,780,568 and WO 02/055469. Particularly suitable purification processes and purification devices for product crystals which contain at least about 80 wt. %, preferably at least about 95 wt. % and particularly preferably at least about 99 wt. % of acidic monomer based respectively on the product crystal, are disclosed in WO 02/055469.

It is further preferred in the process according to the invention that the acidic monomer possess a pH value of less than about 7, preferably less than about 5 and particularly preferably less than about 3. (Meth)acrylic acid is particularly preferred as acidic monomer. The determination of pH value for the acidic monomer and for the Brönsted acid is carried out in aqueous solution according to "*Maβanalyse Theorie und Praxis der klassischen und der Elektrochemischen Titrierverfahren*", Walter de Gruyter & Co. Berlin 1969. The term (meth)acrylic acid is used in this text for the compound with the nomenclature name "methacrylic acid" and "acrylic acid". Of the two compounds acrylic acid is preferred according to the invention.

The invention further concerns a device for the synthesis of an acidic monomer having a double bond, having in fluid conducting association as components:
  i. as a monomer synthesis unit having a gas phase monomer synthesis unit of a liquid phase monomer synthesis unit,
  ii. a quench unit following the gas phase monomer synthesis unit,
  iii. optionally a first purification unit following the liquid phase monomer synthesis unit or the quench unit,
  iv. a first extraction unit, having as components:
    (aa) a starting mixture conduit connected to the liquid phase monomer synthesis unit or to the quench unit or with the optionally available first purification unit,
    (bb) a phase former conduit,
    (cc) an extraction container accommodating the starting mixture conduit and the phase former conduit,
  v. optionally a further extraction unit connected to the first extraction unit or a further purification unit or both.

In a preferred embodiment of the device according to the invention a portion of the extraction unit, preferably of the extraction container and particularly the extraction container, can be cooled. This form is particularly suited for the presently described single step accomplishment of the process according to the invention.

In another embodiment of the device according to the invention this device has, besides a phase boundary portion, preferably the extraction container, a crystallization portion which is separated from this phase boundary portion. In this separated crystallization portion at least a part of this portion can be cooled. Typical crystallization portions are the crystal generators described elsewhere. This form of the device according to the invention is particularly suitable for the presently described two-step and multistep accomplishment of the process according to the invention.

By "fluid conducting" according to the invention is understood that gases or liquids, including suspensions, or mixtures thereof are conducted through corresponding conduits. To this end, pipes, pumps and the like can be used.

According to one preferred embodiment according to the invention of the device for synthesis of the acidic monomer, this device must have a first purification unit following the quench unit.

According to a further preferred embodiment according to the invention of the device for synthesis of the acidic monomer, this device must have a first purification unit following the liquid phase monomer synthesis unit.

According to another preferred embodiment according to the invention of the device for synthesis of an acidic monomer this device must have a further extraction unit connected to the first extraction unit or a further purification unit or both.

It is therefore preferred in the device according to the invention for synthesis of an acidic monomer that the monomer synthesis unit has at least two reactors. All reactors suitable to the person skilled in the art for synthesis of acidic monomers are considered as reactors. In this context are mentioned for example tubular reactors, wall reactors and layer reactors. In the context of the reactor it is preferred that the reactor has a supported transition metal oxide catalyst, which facilitates the synthesis of the acidic monomer which preferably occurs by gas phase oxidation of a hydrocarbon having a double bond. The supported transition metal catalysts can be supported on all materials known to the person skilled in the art. In this context various metals can be mentioned, in particular materials which are inert and ceramic with respect to the reaction conditions during the synthesis of the acid monomer such as steel, mixed oxides and individual oxides of aluminium, silica and titanium, for example rutile and anatase. Particularly preferred transition metal oxide catalysts are the mixed oxides of vanadium, nickel and molybdenum or a mixture of at least two therefrom. In this context reference is particularly made to the details in DE 196 06 877 under step (I) of this disclosure.

In the context of the device according to the invention for synthesis of an acidic monomer it is particularly preferred that at least one of the reactors is a gas phase reactor.

The mostly gaseous reactor product formed in the monomer synthesis unit by means of the at least one, preferably two reactors via the educts and containing the acidic monomer is then transferred into the quench unit. The quench unit is as a rule a quench tower, in which the gaseous reactor product is contacted with water in order to transfer the acidic monomer into a liquid phase in this way.

In a preferred embodiment according to the invention of the device for synthesis of an acidic monomer a purification unit in the form of a distillation column follows the quench unit. In this distillation column the quench product originating from the quench unit is separated to the greatest possible extent by thermal exposure by distillation into its different components, amongst which the acidic monomer. It is furthermore preferred that the distillation column has a column bottom in its lower portion, which is connected to the starting mixture conduit, in order to transfer the bottom-starting mixture into the extraction unit in this way. In this way the bottom mixtures which accumulate during the course of the distillation and are not transported to the upper portion of the distillation column and mostly contain a non-negligible quantity of acidic monomer can be subjected to a further purification, which leads to an increase in efficiency of the device and in particular to an increase of the yield of the acidic monomer.

According to a further embodiment according to the invention of the device for synthesis of an acidic monomer it is preferred that the distillation column has a column head in the upper portion which is also connected with a starting mixture conduit. This serves to conduct to a further purification the mixtures still containing impurities in the head products of the distillation process besides the desired acidic monomer as head starting mixture of an extraction unit and thereby leads to a further efficiency increase of the device for synthesis of an acidic monomer.

In the course of the distillative workup of the quench product formation of oligomers of the acidic monomer can occur, which must be retransformed into acidic monomer by a suitable oligomer-cracking device. Thus, in an embodiment according to the invention of the device for synthesis of the acidic monomer a cracking device for oligomers of the acidic monomer is provided adjacent to the first purification unit. All processes known to the person skilled in the art for cracking of acidic monomers are considered as cracking devices, in this context in particular catalytic dimer- or trimer-cracking devices should be mentioned. It is further preferred that the cracking device has a cracking device bottom in its lower portion, which is connected to the starting mixture conduit, in order to conduct the oligomer starting mixture to the extraction unit in this way.

In another embodiment according to the invention of the device for synthesis of an acidic monomer it is preferred that this device is fitted with a first purification unit following the quench unit, whereby this first purification unit is a crystal generator. The quench product crystallised by the crystallization generator often forms a eutectic mixture during the crystallization, in which the acidic monomer cannot be isolated in the desired quantities. It is therefore preferred that the eutectic starting mixture be transferred via the starting mixture conduit into the extraction unit, in order to be purified there by the process according to the invention. Crystal generators used can be all those known to the person skilled in the art and suitable according to the invention. Layer and suspension crystal generators fall into this category. As suspension crystal generators boiler crystallizers, scratch crystallizers, cool plate crystallizers, crystallization worms, drum crystallizers and the like can be used advantageously, wherein the suspension crystal generator is preferably operated with a downstream wash column. In this context reference is made to the disclosure of WO 99/14181.

The invention further concerns a process for producing an acidic monomer having a double bond, wherein at least one synthesis mixture generated in the reactor and containing the acidic monomer is contacted with water and is, optionally after at least one further workup step, supplied as starting mixture to a process according to the invention for purification of an acidic monomer.

It is also preferred that the process according to the invention for producing an acidic monomer be carried out in at least one reactor by oxidation of a hydrocarbon having at least one double bond. These hydrocarbons can be C2 to C10, preferably C3 to C5 and particularly preferably C3 hydrocarbons. Propylene is particularly preferred as hydrocarbon in the case of production of acrylic acid.

All systems known to the person skilled in the art and apparently suitable are considered as liquid phase monomer synthesis units, in which starting from a hydrocarbon having a double bond as educt in the liquid phase of a solvent, the acidic monomer, preferably already dissolved in a solvent, is obtained by means of transition metal compounds with ligand systems as catalysts.

It is further preferred according to the invention that in the process according to the invention for synthesis of an acidic monomer a device according to the invention for synthesis of an acidic monomer be used.

The invention further concerns an acidic monomer which is obtainable by a process according to the invention for synthesis of an acidic monomer.

The invention furthermore concerns fibres, formed bodies, films, foams, superabsorbent polymers, special polymers for the areas of waste water treatment, dispersion dyes, cosmetics, textiles, leather finishing or paper producing or hygiene articles, at least based on an acidic monomer according to the invention.

In addition the invention concerns the use of the acidic monomers according to the invention in or for producing fibres, formed bodies, films, foams, superabsorbent polymers or hygiene articles, detergents or special polymers for the areas of waste water treatment, dispersion dyes, cosmetics, textiles, leather finishing or paper producing.

The invention is now described in more detail, although not limited, by means of figures and examples.

Figure 1:
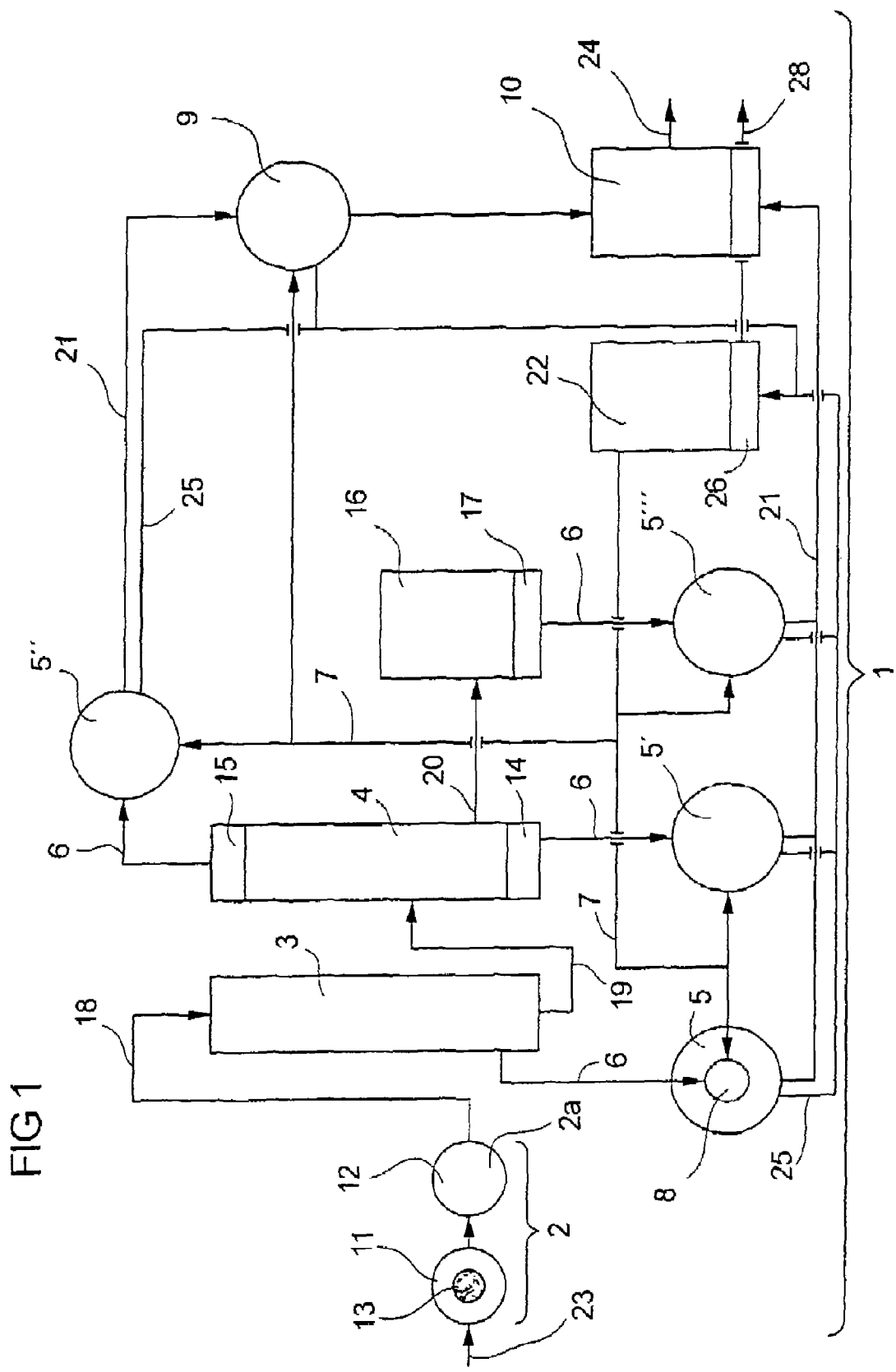
FIG. 1 shows in the form of a flow diagram a schematic assembly of a monomer synthesis device according to the invention with possible extraction units arranged in different positions.

In the monomer synthesis device 1 illustrated in FIG. 1 the necessary educt for the synthesis of the acidic monomer—in the case of acrylic acid, propylene and oxygen—is introduced into a first reactor 11 via an educt inlet 23. The educt mixture is first converted in the case of the acrylic acid synthesis principally into acrolein by a supported transition metal catalyst 13 in a gas phase oxidation reaction in the first reactor 11, in order to then subject this to a further gas phase oxidation into acrylic acid in a further reactor 12. The first reactor 11 and the further reactor 12 form a gas phase monomer synthesis unit 2a as monomer synthesis unit 2. Via a reactor product conduit 18 the reactor product is conducted from the monomer synthesis unit 2 into a quench unit 3. A first extraction unit 5 can be attached to the quench unit 3 via a starting mixture conduit 6, in which extraction unit 5 the quench product is subjected to the workup process according to the invention. It is furthermore possible to supply the quench product via a quench product conduit 19 of a first purification unit 4. The first purification unit 4 can be a crystallization device, a crystallization device with a washing device or a distillation column. In the case where the first purification unit 4 is a distillation column, this distillation column has a column bottom 14 in the lower portion and a column head 15 in the upper portion of the distillation column. A further first extraction unit 5' or 5" can be attached to the column bottom 14 or to the column head 15 or to both by appropriate starting mixture conduits 6. It is furthermore possible that a cracking device 16 for oligomers of the acidic monomers is attached via an oligomer conduit 20 to the first purification unit 4 designed as a distillation column. This cracking device 16 has a cracking device bottom 17, which is connected via a further starting mixture conduit 6 with a further extraction unit 5'''. In the case that the first purification unit 4 is a crystallization unit or a crystallization unit with a washing device, it is further possible that the products containing the acidic monomer in purified form and accumulating in the crystallization device or in the crystallization device with washing device, in particular if these are present as aqueous compositions close to the eutectic point of these compositions, are supplied via the starting mixture conduit 6 to a further first extraction unit 5'. The first purification unit 5 has an extraction container 8, in which besides the starting mixture conduit 6 a phase former conduit 7 discharges. The thus formed extraction unit has in this way phase boundary and crystallization areas together in the extraction container 8. Also the further first extraction units 5, 5', 5" as well as 5'" are supplied via the respective phase former conduits 7 with phase former from the phase former tank 22. The purified product of a further purification unit 10 is supplied via a product/crystal conduit 21 in the first extraction units 5, 5', 5" and 5'". Thereby if possible the product/crystal conduit 21 is interrupted by a further extraction unit 9, in which the crystal phase is subjected to a further purification according to the invention. As further purification unit 10 all devices known to the person skilled in the art and suitable for the further purification can be used. As further purification unit 10 crystallization devices or crystallization devices with washing devices are particularly preferred. The purified acidic monomer from the monomer synthesis device is removed from the further purification unit 10 via a pure product outlet 24. The residues forming in the first extraction unit 5, 5', 5", as well as 5'" can be supplied via a residue conduit 25 to a phase former preparation 26, in which the phase former is recovered and transferred into the phase former tank 23. Residues accumulating during the workup and recovery of the phase former are discharged from the monomer synthesis device 1 via a residue discharger 28.

The following combinations depicted in the monomer synthesis device 1 in FIG. 1 are preferred in detail as embodiments for example for use in further monomer synthesis devices 1: the combination of the quench unit 3 with the first extraction unit 5, the combination of the first purification unit 4 with the first extraction unit 5' in the case that the first extraction unit 5' is a crystallization device or a crystallization device with a washing device; the combination of the first purification unit 4 with the first extraction unit 5' in the case that the first extraction unit 5' is a distillation column with a column bottom 14; the combination of the first purification unit 4 with the first extraction unit 5" in the case that the first purification unit 4 is a distillation column with a column head 15; the combination of the first purification unit 4 with the first extraction unit 5' as per the further first extraction unit 5" in the case that the purification unit 4 is a distillation column with a column bottom 14 and a column head 15; the combination of the first purification unit 4 with the cracking device 16, which has a cracking device bottom 17, in the case that the first purification unit 4 is a distillation column, in connection with the further first extraction unit 5".

Figure 2:
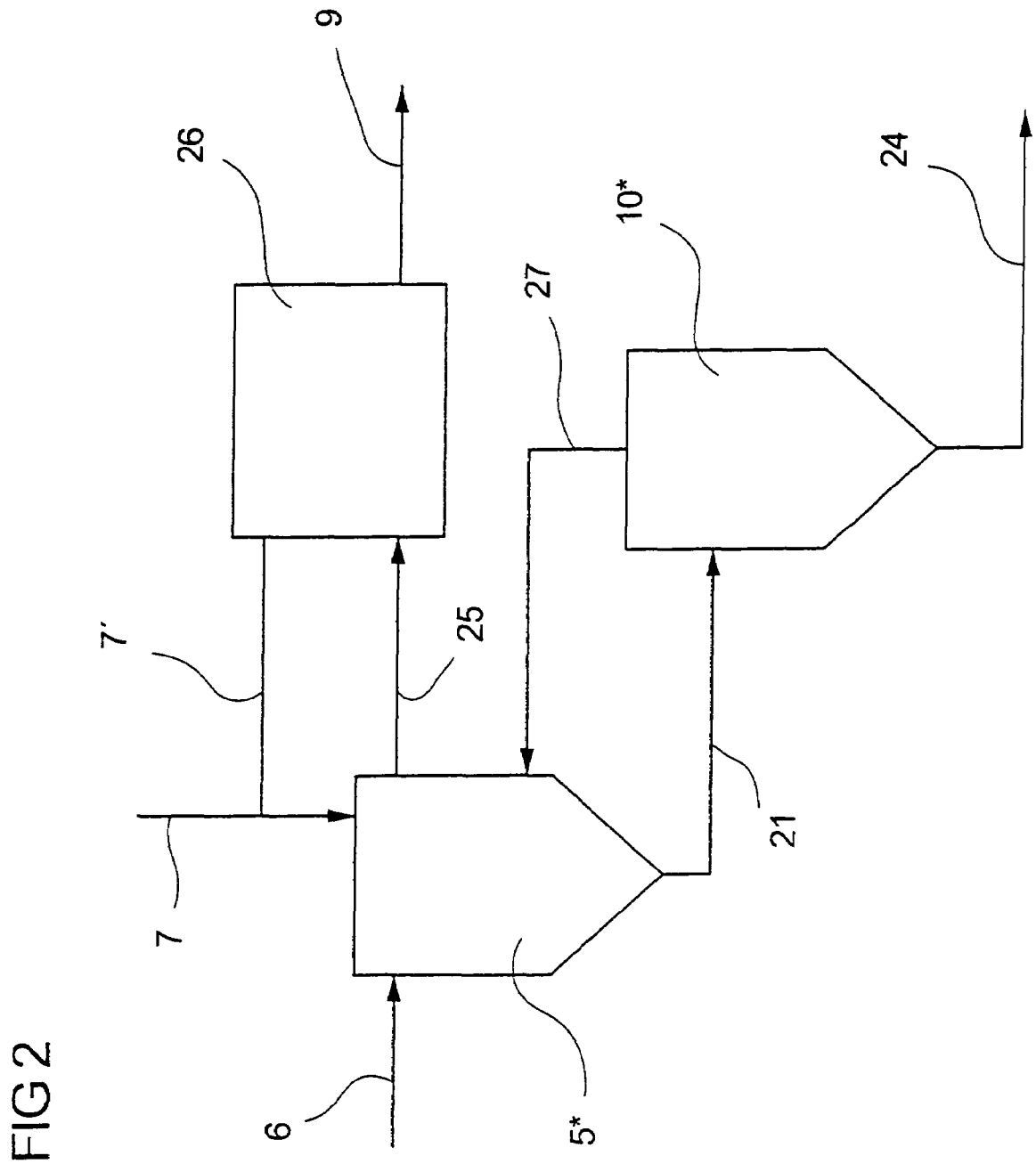
FIG. 2 shows as a flow diagram the combination of an extraction unit according to the invention with a phase former preparation unit and a further purification unit.

FIG. 2 shows an extraction unit 5 which can preferably be used in a monomer synthesis device 1 in different positions shown in FIG. 1, wherein this extraction unit 5 has a further extraction unit 5*, which is combined with a further purification unit 10*. The starting mixture together with the phase former supplied via the phase former conduit 7 is fed via the starting mixture conduit 6 into the further extraction unit 5*, so that acidic monomer contained in the starting mixture can be purified by the process according to the invention. The phase former and as little acidic monomer as possible (less than 20 wt. %, preferably less than 10 wt. % and particularly preferably less than 5 wt. %, respectively based on the mixture discharged through the residue conduit 25) are transferred via the residue conduit 25 into the phase former preparation 26. The phase former obtained in the phase former preparation 26 is supplied again to the first extraction unit 5* via the phase former conduit 7. The crystal phase rich in acidic monomer is transferred via the product/crystal conduit 21 into the further purification unit 10*. This purification unit 10* can be a crystallization device or a crystallization device with a washing device. It can be preferred that the crystals of the acidic monomer be at least partially fused before the introduction of the product/crystal phase into the further purification unit 10. In the further purification unit 10* the crystal phase is further purified, whereby the residue of this purification can be supplied back to the first extraction unit 5* via the purification residue conduit 27 and the purified acidic monomer can be discharged from the further purification unit 10* via the pure product outlet 24.

Figure 3:
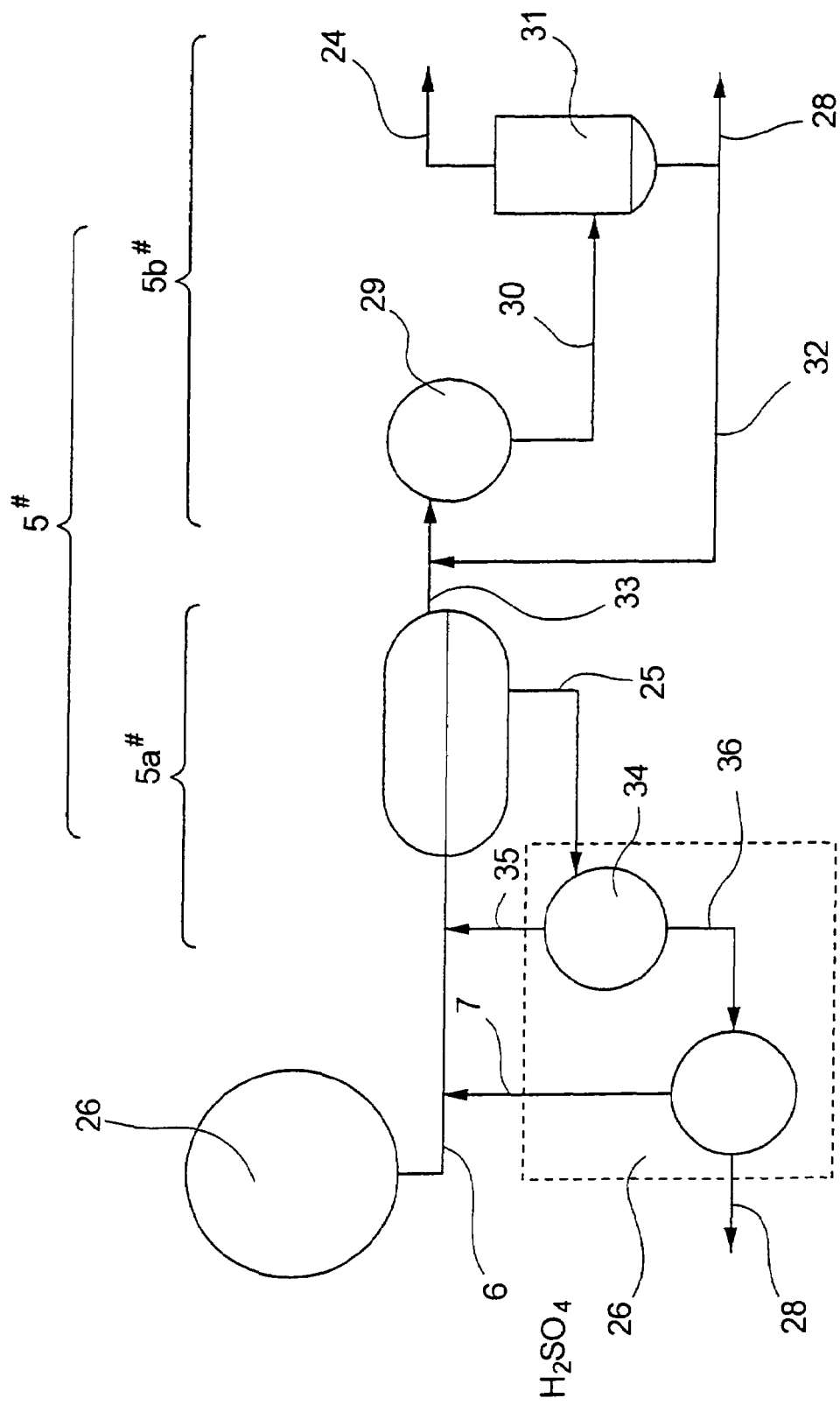
FIG. 3 shows as a flow diagram a further two-step combination of an extraction unit with extraction and crystallization portions separated from each other and a liquid phase monomer synthesis unit.

In FIG. 3 the starting mixture obtained for example in a liquid phase monomer synthesis unit 2b is supplied via the starting mixture conduit 6 with, in the case of the purification of acrylic acid in the range from 60 to 80 wt. % acrylic acid, into an extraction unit 5#. The extraction unit 5# has a phase boundary portion 5a#, from which the product richer phase, which is preferably poorer in phase former, is conducted via a product phase conduit 33 into a crystallization area 5b# separated from the phase boundary portion 5a# and with a crystallizer 29 for generating a crystal suspension. The crystal suspension passes via a crystal suspension conduit 30 into a washing column 31, in which the product is isolated and discharged via the pure product outlet 24 and can optionally be supplied to a further purification unit 10. The mother liquor accumulating in the crystallizer 29 during the separation in the washing column 31 can be recovered via a mother liquor conduit 32 or at least partially removed via the residue discharger 28. The product-poor and phase former-rich residue from the phase boundary portion 5a# of the phase former preparation 26 can be supplied via the residue conduit 25 and the there-prepared phase former—preferably sulphuric acid—from there fed into the phase former conduit 7 and the residue accumulated during the preparation of the phase former removed via the residue discharger 28. The phase former preparation 26 preferably has a first flash container 34 connected with the consumed phase former and further residues-conducting residue conduit 25. In the first flash container 34 the low-boiling components, mostly water and acrylic acid, evaporated from the residue and supplied back via the recyclables conduit 35 to the phase boundary portion 5a#. The high-boiling fraction containing mostly phase former and residue is supplied via a high-boiling conduit 36 to a further flash container 37 which mostly operates at higher temperatures. In this further flash container 37 the phase former is isolated as a low-boiling component and supplied via the phase former conduit 7 to the phase former portion 5a#. The high-boiling fraction is discharged through a residue discharger 28.

EXAMPLES

1. Phase Separation A

Into a double walled laboratory glass vessel with a capacity of 1.5 l maintained at 20° C. were placed and stirred with a magnetic stirrer 724 g of a mixture with composition according to Table 1. Then 226 g phase former (96% sulphuric acid) were added. Following the addition a phase separation was observed. The composition of the individual phases are given in Table 1.

TABLE 1

| | Educt Content in Mass % | Upper Phase Content in Mass % | Lower Phase Content in Mass % |
|---|---|---|---|
| Acrolein | 0.025 | <0.01 | <0.01 |
| Acetic acid | 3.146 | 3.091 | 1.994 |
| Furfuraldehyde | 0.024 | 0.023 | <0.01 |
| Benzaldehyde | 0.028 | 0.042 | <0.01 |
| Propionic acid | 0.013 | 0.036 | 0.042 |
| Protoanemonin | 0.017 | 0.019 | <0.01 |
| Acrylic acid | 65.925 | 93.100 | 25.400 |
| Acrylic acid dimer | 0.388 | 0.777 | 0.353 |
| Maleic acid anhydride | 0.100 | 0.422 | 0.529 |
| Water | 30.200 | 3.700 | 36.6 |
| Sulphuric acid | — | 2.900 | 36.3 |

2. Phase Separation B

The experiment was repeated as for Phase Separation A, with the difference that 874 g of a mixture with composition according to Table 2 and 305 g of 70% aqueous sodium hydrogensulfate solution were used as phase former. The composition of the phases produced is given in Table 2.

TABLE 2

| | Educt Content in Mass % | Upper Phase Content in Mass % | Lower Phase Content in Mass % |
|---|---|---|---|
| Acrolein | 0.025 | 0.011 | <0.001 |
| Acetic acid | 3.146 | 3.400 | 0.700 |
| Furfuraldehyde | 0.024 | 0.023 | 0.001 |
| Benzaldehyde | 0.028 | 0.026 | <0.001 |
| Propionic acid | 0.013 | 0.018 | 0.009 |
| Protoanemonin | 0.017 | Not mentioned | Not mentioned |
| Acrylic acid | 65.925 | 68.100 | 8.000 |
| Acrylic acid dimer | 0.388 | 0.500 | <0.001 |
| Maleic acid anhydride | 0.100 | 0.600 | 0.300 |
| Water | 30.200 | 23.700 | 47.600 |
| Sodium hydrogensulfate | — | 8.700 | 43.000 |

3. Extraction-Crystallization Experiment (Single-Step)

Into a double-walled laboratory glass vessel with a capacity of 250 ml maintained at 20° C., 170 g of a mixture with a composition according to Table 3 (educt) were stirred with a magnetic stirrer. Then 55 g of 96% sulphuric acid were added as phase former with formation of two phases. The temperature was then reduced until crystals formed at 6.8° C. The temperature was further reduced to 5.4° C. until crystals stopped forming. The crystals of the thus obtained crystal phase were isolated by means of a vacuum suction filter and washed with 102 g 99.8% acrylic acid. The different compositions are given in Table 3. The crystallization out of the principally acrylic acid-containing phase was so complete that a residue formed in the form of an aqueous/organic suspension. Using the vacuum suction filter this suspension could be easily separated from the crystals which formed a filter cake. After washing with 99.8% acrylic acid crystals were obtained with a yield of 51% based on the acrylic acid used in the educt.

TABLE 3

| Description | Unit | Educt | Crystals after washing | Crystals before washing | Residue (aq./org. Phase) |
|---|---|---|---|---|---|
| water | wt. % | 33.7 | 0.8 | 4.4 | 39.3 |
| Acrylic acid | wt. % | 62.6 | 97.6 | 83.3 | 24.5 |
| Acetic acid | wt. % | 3.0 | 0.2 | 1.2 | 2.5 |
| Propionic acid | wt. % | 0.012 | <0.01 | 0.014 | 0.06 |
| Acrylic acid dimer | wt. % | 0.277 | 11 mg/kg | 0.3 | 0.2 |
| Maleic acid anhydride | wt. % | 0.17 | 38 mg/kg | 0.1 | 0.5 |
| Furfuraldehyde | wt. % | 0.0221 | <0.01 | <0.01 | 0.038 |
| Benzaldehyde | wt. % | 0.0272 | <0.01 | 0.021 | 0.017 |
| Acrolein | wt. % | 0.033 | <0.01 | <0.01 | 0.014 |
| Protoanemonin | wt. % | 0.0158 | <0.01 | <0.01 | 0.018 |
| Sulphuric acid | wt. % | — | 1.3 | 2.3 | 34.5 |

4. Crystallization/Layer Crystallization (Two-Step)

Into a double-walled laboratory glass vessel with capacity of 4 l maintained at 10° C. were placed 2 l of an educt obtained analogously to Example 1 as upper phase. The composition of the educt is given in Table 4. A cool finger with a temperature of 10° C. was placed in the centre of the laboratory glass vessel, whereby the cool finger was previously dipped in 99.8% acrylic acid to wet the cool finger surface. Then the cool finger and the double-walled lab vessel were cooled to a temperature of 4° C., so that a crystal layer began to form on the cool finger surface. The cool finger was further cooled at a rate of 0.15° C./min to −8° C. The mother liquor, depleted in acrylic acid, was discharged and the crystals from the cold finger analysed. Then the cold finger was warmed at a rate of 0.2° C./min to 2° C., in order to further purify the crystal layer on the cold finger by sweating. The compositions of the crystals of the individual steps are given in Table 4.

TABLE 4

| Fractions | Amount Mass (g) | Determination | Sulphuric Acid w (%) | Acrylic Acid w (%) | Acrylic Acid dimer w (%) | Acetic Acid w (%) | Maleic Acid w (%) | Furfuraldehyde w (%) | Benzaldehyde w (%) | Propionic Acid w (%) | Water w (%) |
|---|---|---|---|---|---|---|---|---|---|---|---|
| Feed | 1982 | Analysis | 2.000 | 88.000 | 1.400 | 2.400 | 0.400 | 0.020 | 0.044 | 0.020 | 11.700 |
| Mother liquor | 1891 | Balanced | 2.034 | 88.357 | 1.427 | 2.436 | 0.408 | 0.02 | 0.045 | 0.02 | 11.908 |
| Crystallisate before sweating | 82 (balanced) | Balanced | 1.433 | 89.426 | 0.922 | 1.822 | 0.250 | 0.012 | 0.019 | 0.018 | 8.174 |

TABLE 4-continued

| Fractions | Amount Mass (g) | Determination | Sulphuric Acid w (%) | Acrylic Acid w (%) | Acrylic Acid dimer w (%) | Acetic Acid w (%) | Maleic Acid w (%) | Furfuraldehyde w (%) | Benzaldehyde w (%) | Propionic Acid w (%) | Water w (%) |
|---|---|---|---|---|---|---|---|---|---|---|---|
| Sweat fraction | 67 | Analysis | 1.700 | 88.000 | 1.100 | 2.000 | 0.300 | 0.014 | 0.023 | 0.019 | 9.600 |
| Crystallisate after sweating | 14 | Analysis | 0.200 | 96.000 | 0.100 | 1.000 | 0.020 | 0.001 | 0.002 | 0.014 | 1.600 |

LIST OF CHARACTERS

| | |
|---|---|
| 1 | monomer synthesis device |
| 2 | monomer synthesis unit |
| 3 | quench unit |
| 4 | first purification unit |
| 5 | first extraction unit |
| 6 | starting mixture conduit |
| 7 | phase former conduit |
| 8 | extraction container |
| 9 | further extraction unit |
| 10 | further purification unit |
| 11 | first reactor |
| 12 | further reactor |
| 13 | supported transition metal oxide catalyst |
| 14 | column bottom |
| 15 | column head |
| 16 | cracking device |
| 17 | cracking device bottom |
| 18 | reactor product conduit |
| 19 | quench product conduit |
| 20 | oligomer conduit |
| 21 | product/crystal conduit |
| 22 | phase former tank |
| 23 | educt inlet |
| 24 | pure product outlet |
| 25 | residue conduit |
| 26 | phase former preparation |
| 27 | purification residue conduit |
| 28 | residue discharger |
| 29 | crystallizer |
| 30 | crystal suspension conduit |
| 31 | washing column |
| 32 | mother liquor conduit |
| 33 | product phase conduit |
| 34 | first flash container |
| 35 | recyclables conduit |
| 36 | high-boiling conduit |
| 37 | further flash container |

What is claimed is:

1. A process for purification of an acidic monomer having a double bond, comprising the steps of:
 (a) providing a starting mixture, containing as starting mixture components, respectively based on the starting mixture,
  (a1) at least about 5 wt.% of the acidic monomer and either
  (a2) at least about 0.01 wt.% water, or
  (a3) at least about 0.01 wt.% of at least one starting mixture component comprising impurities which are different to the acidic monomers with the exception of water, or
  (a2) and (a3)
   wherein the sum of the wt.% proportions of the starting mixture components gives respectively 100 wt.%;
 (b) adding a phase former or a salt of this phase former or a mixture of both to obtain a purification mixture, from which
 (c) at least one first phase and an at least one further phase distinguished from the first phase by means of a phase boundary form a phase system;
 (d) lowering of the temperature of the phase system; wherein
 (e) in one of the phases of the phase system a product crystal containing at least about 50 wt.% of one of the starting mixture components is formed in addition to another starting mixture component as a crystal system;
 (f) isolating the product crystals wherein the acidic monomer is (meth) acrylic acid.

2. The process according to claim 1, wherein the temperature is lowered in only one phase of the phase system.

3. The process according to claim 2, wherein the temperature is lowered in the most monomer-rich phase of the phase system.

4. The process according to claim 1, wherein the acidic monomer has a pH value of less than about 7.

5. The process according to claim 1, wherein the phase former is a Bröonsted acid with a pH value of less than 6 or a salt of a Bröonsted acid or a mixture thereof.

6. The process according to claim 5, wherein the Bröonsted acid is sulphuric acid or one of its salts or a mixture thereof.

7. The process according to claim 1, wherein the phase former is liquid at the time of addition.

8. The process according to claim 1, wherein the purification mixture contains the phase former in a quantity in the range from about 1 to about 80 wt.%, based on the purification mixture.

9. The process according to claim 1, wherein at least one part of the phase former is recovered after formation of the phase systems and reused in step (b) of the staffing mixture.

10. The process according to claim 1, wherein the crystal system or the isolated monomer crystal or both are subjected to at least one further purification step.

* * * * *

UNITED STATES PATENT AND TRADEMARK OFFICE
CERTIFICATE OF CORRECTION

PATENT NO. : 7,495,129 B2  Page 1 of 1
APPLICATION NO. : 10/541647
DATED : February 24, 2009
INVENTOR(S) : Torsten Balduf et al.

It is certified that error appears in the above-identified patent and that said Letters Patent is hereby corrected as shown below:

Title Page,
Foreign Application Priority Data, "103 01 040" should read -- 103 01 0408 --.

Column 16,
Line 43, "is a Bröonsted acid" should read -- is a Brönsted acid --.

Column 16,
Line 44, "of a Bröonsted acid" should read -- of a Brönsted acid --.

Column 16,
Line 45, "wherein the Bröonsted" should read -- wherein the Brönsted --.

Signed and Sealed this

Twenty-fifth Day of August, 2009

David J. Kappos
*Director of the United States Patent and Trademark Office*